United States Patent [19]

Coffey et al.

[11] Patent Number: Plant 6,627

[45] Date of Patent: Feb. 21, 1989

[54] AVOCADO TREE CALLED BARR DUKE

[75] Inventors: Michael D. Coffey, Riverside; Fred B. Guillemet, Chino, both of Calif.

[73] Assignee: The Regents of the University of California, Berkeley, Calif.

[21] Appl. No.: 99,439

[22] Filed: Sep. 21, 1987

[51] Int. Cl.[4] ..... A01H 5/03

[52] U.S. Cl. ..... Plt./44

[58] Field of Search ..... Plt./44

*Primary Examiner*—Robert E. Bagwill

*Attorney, Agent, or Firm*—Townsend and Townsend

[57] ABSTRACT

A new and distinct rootstock variety of avocado tree characterized by its high yield resistance to Phytophthora root rot caused by *Phytophthora cinnamomi.* This variety has a high level of resistance comparable to the 'Duke 7' rootstock variety. It is also characterized under some field conditions by producing a somewhat smaller tree, when grafted with a 'Haas' scion, than that typical of a 'Duke 7' rootstock.

2 Drawing Sheets

DESCRIPTION

This invention relates to a new and distinct rootstock variety of avocado tree (*Persea americana* var. drymifolia) designated 'Barr Duke'.

'Barr Duke' is a Mexican avocado rootstock. It is a seedling of 'Duke 6' and has been tested at the University of California, Riverside and at South Coast Field Station, Irvine, Calif. for resistance to Phytophthora root rot caused by *Phytophthora cinnamomi.* It has also been tested for root rot resistance in various avocado grooves in southern California. 'Barr Duke' was initially tested in a nutrient solution tank which survived the severe root rot test and was then transplanted to infested soil in the greenhouse. The selection showed promise as a rootstock for root rot resistance and additional materials of the selection were propagated asexually for further greenhouse tests and for resistance tests in field plots. Over a period of seven years 'Barr Duke' has demonstrated excellent growth in diseased sites. Further asexual reproduction of 'Barr Duke' demonstrates that the variety remains consistent in the characteristics that distinguish it.

Figure 1:
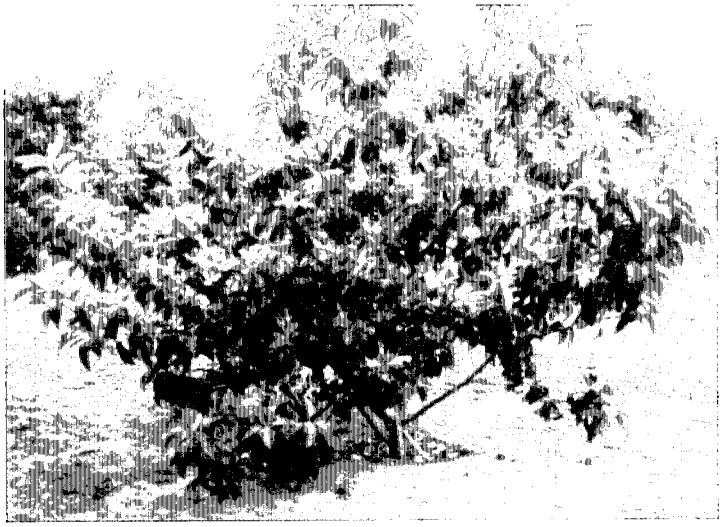
FIG. 1 shows the general shape and color of the 'Barr Duke' selection.
Figure 2:
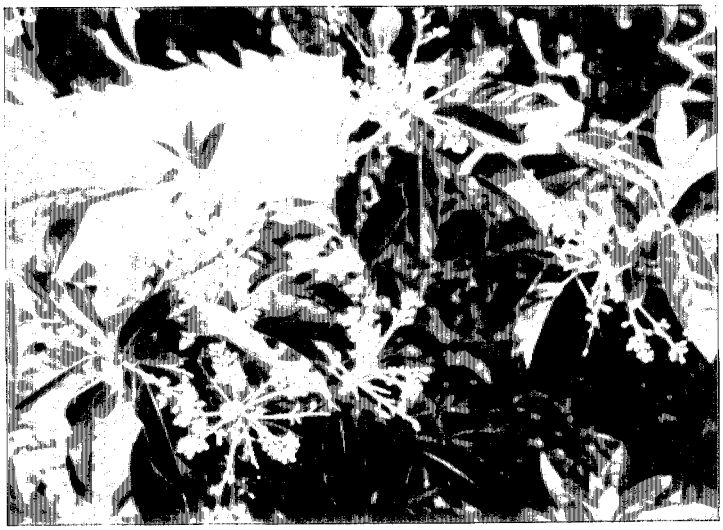
FIG. 2 shows the foliage and flowers in more detail.
Figure 3:
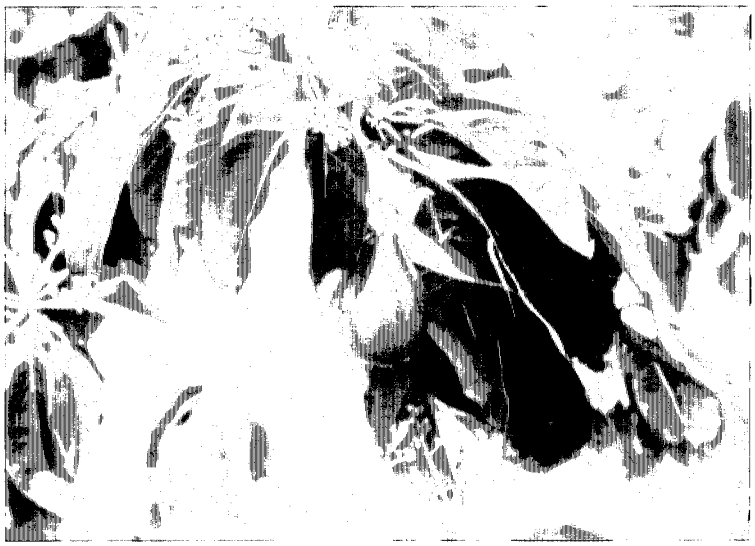
FIG. 3 shows the mature green fruit of the 'Barr Duke' variety.

'Barr Duke' has three primary characteristics that distinguish it. It has high field resistance to Phytophthora root rot. It is a Mexican variety and is well-adapted to California conditions. When used as a rootstock, under some growing conditions, it reduces the size of the Hass scion variety.

Resistance to *Phytophthora cinnamomi* has been tested in many experiments with 'Barr Duke' in the field. 'Barr Duke' has consistently proved to be resistant, at a level comparable to the 'Duke7' rootstock. In an extremely severe test where the trees were deliberately inoculated with Phytophthora at planting time, 'Barr Duke' was evaluated as producing growth comparable to that with 'Barr Duke' not inoculated with Phytophthora.

It is a less vigorous grower than 'Duke 7', 'G755C' or 'Thomas', with or without Phytophthora root rot being present.

TREES AND FOLIAGE

'Barr Duke', as is the case with the majority of avocado varieties, does not have distinctive foliage. The leaves have a distinct anise scent when crushed, which typifies the Mexican horticultural race.

FRUIT

Ovate; about 150 grams; smooth skin. Flesh about like 'Zutano'. With reference to the Munsell Color Charts typically 'Barr Duke' has a skin color (strong yellow green, Munsell Hue 2.5 GY 6/8) similar to the variety 'Duke'. The season is about August through September in Southern California.

The following chart represents visual ratings of the 'Barr Duke' variety compared with other root rot resistant varieties according to observations made at the South Coast Field Station on Aug. 14, 1986.

| SELECTION | # PLANTED | # SYMPTOMS | % HEALTHY | AVE. STAGE |
|---|---|---|---|---|
| BARR DUKE | 10 | 1 | 90 | 0.2 |
| G755A | 10 | 1 | 90 | 0.4 |
| THOMAS | 10 | 1 | 90 | 0.6 |
| G755C | 10 | 3 | 70 | 1.4 |
| G6 PARENT | 10 | 4 | 60 | 1.4 |
| TORO CANYON | 10 | 5 | 50 | 2.4 |
| D9 | 10 | 5 | 50 | 2.8 |
| DUKE 7 | 10 | 6 | 40 | 2.2 |
| G755B | 10 | 6 | 40 | 2.4 |
| G1033 | 10 | 8 | 20 | 4.3 |
| TOPA-TOPA | 10 | 8 | 20 | 6.1 |
| BORCHARD | 10 | 9 | 10 | 7.4 |

We claim:

1. The new and distinct rootstock variety of avocado tree herein described and illustrated and identified by the characteristics enumerated above.

* * * * *